United States Patent [19]

Obayashi et al.

[11] Patent Number: 5,298,241
[45] Date of Patent: Mar. 29, 1994

[54] SPIROGYRA CONTROLLING AND DEODORANT COMPOSITION

[75] Inventors: Hisashi Obayashi, Shiga; Yasuhiro Matsumura, Osaka; Akitoshi Mochida, Chiba, all of Japan

[73] Assignee: Takeda Garden Product Co., Ltd., Tokyo, Japan

[21] Appl. No.: 862,175

[22] Filed: Apr. 2, 1992

Related U.S. Application Data

[62] Division of Ser. No. 556,182, Jul. 23, 1990, Pat. No. 5,149,534.

[30] Foreign Application Priority Data

Jul. 24, 1989 [JP] Japan .............................. 192088/1989

[51] Int. Cl.⁵ .......................... A61L 9/00; A61L 2/16; A61K 35/78
[52] U.S. Cl. ................................. 424/76.1; 424/195.1; 424/405; 424/489
[58] Field of Search ...................... 424/195.1, 405, 489, 424/76.1, 837

[56] References Cited

U.S. PATENT DOCUMENTS 4,059,695 11/1977 Hirosaki et al. ................... 424/195.1
5,149,534 9/1992 Obayashi et al. ................. 424/195.1

FOREIGN PATENT DOCUMENTS 59-44396 3/1984 Japan.
63-230169 9/1988 Japan.
64-27559 1/1989 Japan.
249516 2/1990 Japan.
2112286 7/1983 United Kingdom.

OTHER PUBLICATIONS

Walter H. Lewis et al., "Plants Affecting Man's Health," Medical Botany, John Wiley & Sons, New York (1977).

Primary Examiner—John W. Rollins
Attorney, Agent, or Firm—Wegner, Cantor, Mueller & Player

[57] ABSTRACT

A spirogyra controlling and deodorant composition contains the cortex of Japanese cedar and/or Japanese cypress or an extract thereof. This serves to suppress or prevent the occurrence of spirogyra and maladous odor in water or on moist surface in fish rearing aquarium, pond, marsh, water culture or the like.

4 Claims, 1 Drawing Sheet

SPIROGYRA CONTROLLING AND DEODORANT COMPOSITION

This application is a divisional of Ser. No. 07/556,182, filed Jul. 23, 1990, now U.S. Pat. No. 5,149,534.

BACKGROUND OF THE INVENTION

1. Field of the Invention

The present invention relates to a spirogyra controlling and deodorant composition that serves well for the purpose of suppressing or preventing the occurrence of spirogyra and maladous odor in water or on moist surface in fish rearing aquarium, water culture and by mulching pond and marsh, etc.

2. Prior art

In fish rearing, there is no effective means of controlling spirogyra and preventing maladous odor.

In water culture, there is a prior art method of controlling spirogyra, as illustrated in FIG. 3.

In this method, artificial urethane resin medium (2) is placed above a solution chamber (1); solution (3) is circulated by pumping it from a solution tank (4) to the solution chamber (1) by means of a circulatory pump (8); solution (3) is then fed through the solution chamber (1) to a grown plant (6) retained by the net-like retainer (5) of artificial medium (2), wherein the solution surface around the base of the grown plant (6) is covered with wool pills (7) for shading, to prevent the photosynthesis of spirogyra and thus suppress its occurrence.

The prior art method described above poses the following problems, 1) through 3).

1) The occurrence of spirogyra is suppressed only around the shaded base portion. Spirogyra that has occurred at the unshaded portion midway in the circulation path of the solution (3) is transferred, due to the circulation of solution (3), and clings to the net-like retainer (5) of artificial medium (2), adding maladous odor to the grown plant (6).

2) To remove spirogyra clinging to the net-like retainer (5) of artificial medium (2), it is necessary to remove the artificial medium (2) from the solution chamber (1). Also, clogging of the circulation path of the solution (3) by spirogyra necessitates disassembly of the circulation path unit. These operations hamper easy cleaning.

3) Since wool pills (7) are degreased and begin to absorb water in about 24 hours, and since spirogyra occurs on the surface of the pills (7) that have absorbed water, the pills must be renewed frequently, an undesirable requirement in that maintenance is troublesome and cost is high.

The object of the present invention is to provide a spirogyra controlling and deodorant composition capable of perfectly controlling spirogyra and maladous odor and retaining its controlling performance for a long time.

SUMMARY OF THE INVENTION

The spirogyra controlling and deodorant composition of the present invention is characterized by the containment of the cortex of Japanese cedar and/or Japanese cypress or an extract thereof.

The spirogyra controlling and deodorant composition may be prepared in a feathery form by cutting the cortex of Japanese cedar or Japanese cypress in accordance with the method described in Japanese Patent Publication Open to Public Inspection No. 49516/1990. However, this is not to be construed as limitative. Accordingly, it may take a powder form as obtained by milling the cortex of Japanese cedar and/or Japanese cypress using a rotary mill. It may also be formed into a plate, rod, block or another form directly or after mixing in rock wool etc , or may be in a lump form. Also acceptable are an extract obtained from the crushed Japanese cedar and/or Japanese cypress containing the cortex of Japanese cedar and/or Japanese cypress by a conventional compression or steam distillation, a dry powder obtained from the extract, a plate, rod, block or another form of product obtained by forming the extract.

The Japanese cedar and Japanese cypress for the present invention are exemplified by Cryptomeria japonica and Chamaecyparis obtusa, respectively. Examples also include varieties thereof.

Also, the spirogyra controlling and deodorant composition comprising the cortex of Japanese cedar and/or Japanese cypress of the present invention may contain a bleacher, a binder, a fertilizer component, a trace element, an activator, a fungicide, an insecticide, a miticide, etc. as desired. desired.

Any bleacher can be used, as long as it is capable of preventing the coloring of plant cultivation solution or fish rearing water due to use of the spirogyra controlling and deodorant composition of the present invention. It is preferable to use activated charcoal.

Although it is impossible to generally specify the amount of bleacher used, it is normally preferable to use it in the range of from about 5 to 30 parts to 100 parts of the cortex of Japanese cedar and/or Japanese cypress (figures for parts are by weight; the same applies below.)

The binder is used in forming the spirogyra controlling and deodorant composition of the present invention into a plate, rod, block or another form. Examples of the binder include vinyl acetate resins (solutions, emulsions), polyvinyl acetate-polyethylene copolymer resins, polyacrylic acid resins and polyacrylic acid-starch copolymers.

Although it is impossible to generally specify the amount of binder used, it is normally about 5 to 30 parts to 100 parts of the cortex of Japanese cedar and/or Japanese cypress.

Examples of the fertilizer component are urea, ammonium sulfate, ammonium nitrate, ammonium phosphate dibasic, ammonium phosphate monobasic, potassium nitrate, potassium phosphate dibasic, potassium phosphate monobasic, potassium hydroxide, nitrogenous fertilizer, phosphatic fertilizer, potassic fertilizer.

Although it is impossible to generally specify the amount of the fertilizer component used, it is normally about 0.006 parts to 0.1 parts to 100 parts of the cortex of Japanese cedar and/or Japanese cypress.

Examples of the trace element are $MgSO_4$, $MnSO_4$, boric acid, EDTA-Fe, EDTA-Mg, $Cu_2SO_4$, $ZnSO_4$, ammonium molybate or the like.

Although it is impossible to generally specify the amount of the trace element used, it is normally about 0.001 parts to 0.015 parts to 100 parts of the cortex of Japanese cedar and/or Japanese cypress.

Examples of the activator are vitamin $B_1$, vitamin $B_6$, nicotinic-acid amide, choline chloride, gibberellin, benzyladenine, iron chloride, EDTA-Fe or the like.

Although it is impossible to generally specify the amount of the activator used, it is normally about 0.005 parts to 0.05 parts to 100 parts of the cortex of Japanese cedar and/or Japanese cypress.

The fungicide is not limitative, but benomyl, triforine, TPN, maneb, streptomycin or the like are listed as examples of the fungicide.

The insecticide is also not limitative, but acephate, permethrin, MEP, malathon, pyrethrin, resmethrin or the like are listed as examples of the insecticide.

The miticide is also not limitative, but kelthan, fenbutatin oxide, hexythiozox, clofentezine or the like are listed as examples of the miticide.

Although it is impossible to generally specify the amount of each of the fungicide, insecticide and miticide used, it is normally about 0.01 parts to 1.0 parts to 100 parts of the cortex of Japanese cedar and/or Japanese cypress.

A mode of preferred use of the present invention is as follows: For example, when this composition is placed as a filtering material midway in the circulation path of water in a fish aquarium or pond or midway in the circulation path of a solution for water culture, the occurrence of spirogyra and maladous odor in the circulating water or solution is suppressed for a long time.

Furthermore, the occurrence of spirogyra is suppressed around the spirogyra controlling composition comprising the cortex of Japanese cedar and/or Japanese cypress.

For these reasons, when this composition is mixed, for example, in artificial medium for water culture the occurrence of spirogyra on the surface of the artificial medium is suppressed.

Also, when the cortex of Japanese cedar and/or Japanese cypress is mixed in a urethane or rockwool bed for water culture in a ratio of about 10% or more, or when it is shaped into flakes and used for a bed as a substitute for urethane or rockwool, the occurrence of spirogyra at the plant growing portion is suppressed, which permits cultivation of radishes, red-and-white radishes, Japanese honeworts and other plants without malodor.

Also, the rod formed from the spirogyra controlling and deodorant composition of the present invention in the presence of a binder can serve as a tree fern substitute for use as a support for vines. The tree fern substitute comprising the cortex of Japanese cedar and/or Japanese cypress is free of the occurrence of spirogyra and maladous odor. Moreover, when this tree fern substitute is formulated with the fertilizer component, trace element, activator and other materials described above, plant growth is facilitated, since roots develop into inner spaces of the tree fern substitute material and absorb these plant nutrients.

The spirogyra controlling and deodorant composition of the present invention can easily be produced by mixing (preferably uniformly) one or more of the above-mentioned components chosen as desired into the shredded or crushed Japanese cedar and/or Japanese cypress containing at least cortex thereof or an extract thereof, the essential constituent of the present invention, in accordance with a method known per se.

Effects of the invention

The present invention has the following effects, (1) through (3):

(1) In water culture, no malodor is caused on the grown plant, since the occurrence of spirogyra in the solution is suppressed.

(2) Since the occurrence of spirogyra is suppressed, cleaning operation of the circulation path for the artificial medium and solution can be simplified in water culture, and cleaning operation for the aquarium, water circulation path etc. can be simplified in fish rearing.

(3) Since the spirogyra controlling and deodorant composition of the present invention retains its controlling performance for a long time, frequent renewal is unnecessary, which simplifies maintenance.

To substantiate the effects described above, the present invention is hereinafter described in more detail by means of the following examples and experiments.

EXAMPLES 1 AND 2

Figure 1:
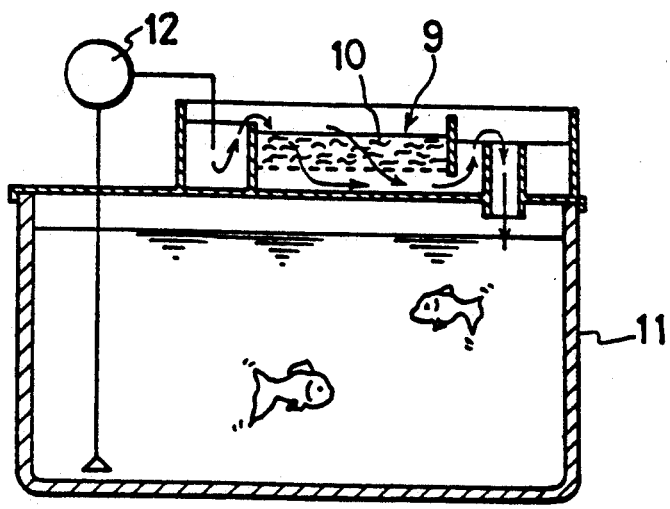
FIG. 1 is a schematic explaining the experimental method of Experimental Example 1.

A feathery material obtained by cutting the cortex of Japanese cedar into a feathery form according to the method described in Japanese Patent Publication Open to Public Inspection No. 49516/1990, and another feathery material obtained by treating the cortex of Japanese cypress in the same manner as above, were mixed uniformly in a ratio of 1 to 1 to yield a spirogyra controlling composition for Example 1.

To 100 parts by weight of the spirogyra controlling composition of Example 1, 30 parts by weight of activated charcoal, as a decoloring agent, was added for Example 2.

EXAMPLE 3

A feathery material obtained by cutting the cortex of Japanese cedar into a feathery form and another feathery material obtained by treating the cortex of Japanese cypress in the same manner as above were mixed uniformly in a ratio of 1 to 1. To 70 parts by weight of this mixture were added 20 parts by weight of a binder (Mitsui Petrochemical Industries, Ltd.) and 10 parts by weight of activated charcoal (Takeda Chemical Industries, Ltd.), followed by kneading in a mixer. The resulting mixture was placed in a mold and dried by heating at 160° C. for 15 minutes. This formed product was sprayed with SA-22 (resin: Takeda Chemical Industries, Ltd.) and dried by heating at 130° C. for several minutes.

EXAMPLES 4 THROUGH 6

A 60-mesh powdery material obtained by milling the cortex of Japanese cedar using a rotary mill and another powdery material obtained by milling the cortex of Japanese cypress in the same manner as above were mixed uniformly in a ratio of 1 to 1. This mixture was mixed with urethane resin to produce a medium in the form of 3 cm cubic block for water culture. Added to whole the block medium was 3% by weight of powdered cortex of Japanese cedar and/or Japanese cypress for Example 4, 5% by weight thereof for Example 5, 10% by weight thereof for Example 6.

EXAMPLE 7

100 parts of rotten Japanese cypress (mixture of skin, sawdust, leaves and branches) was cut and crushed by cutter mill. This cut and crushed rotten Japanese cypress was subjected to water vapor distillation by passing water vapor of 2 atmospheric pressure (135° C.) for 3 hours. As a result, obtained extract was 2.5%.

EXAMPLE 8

100 parts of the skin of Japanese cedar was crushed. This crushed skin was subjected to water vapor distillation by passing water vapor of 4 atmospheric pressure (155° C.) for 2 hours. As a result, obtained extract was 3.2%.

EXAMPLE 9

100 parts of the skin of Japanese cypress was crushed by cutter mill. The crushed skin was subjected to water vapor distillation by passing water vapor of 5 atmospheric pressure (163° C.). As a result, obtained extract was 2.4%.

EXAMPLE 10

100 parts of the sawdust of Japanese cypress was subjected to water vapor distillation by passing water vapor of 4 atmospheric pressure (157° C.) for 3.5 hours. As a result, obtained extract was 3.2%.

EXAMPLE 11

100 parts of the chips of Japanese cedar was crushed by knife mill. The crushed chips was compressed with the weight of 7 tons/cm$^2$ for 3 hours. As a result, obtained extract was 1.8%.

EXPERIMENTAL EXAMPLE 1

The spirogyra controlling composition of Examples 1, 2 and 3 were assessed as to spirogyra controlling performance in comparison with glass wool, for Comparative Example 1 when rearing goldfish.

The experiment was conducted as illustrated in FIG. 1. Specifically, the composition of Example 1, 2 or 3 or Comparative Example 1, in an amount of 100 g as filtering material (10), was packed in the filter (9). To the aquarium (11) containing 30 l of tap water, 100 ml of spirogyra-containing water was added. The water in the aquarium (11) was circulated through the filtering material (10) by means of the circulatory pump (12) for 5 consecutive weeks.

Throughout the experiment period, ten goldfish were kept in the aquarium (11) and fed with commercially available fish food every morning.

Spirogyra controlling performance was rated by visually monitoring the state of occurrence or development of spirogyra once weekly.

The results of assessment are shown in Table 1.

As seen in Table 1, spirogyra occurred and showed noticeable development in Comparative Example 1, while it did not occur at all in Example 1, 2 or 3, even after 5 weeks.

This finding demonstrates that the cortex of Japanese cedar and/or Japanese cypress possesses high capability for spirogyra control in fish rearing.

After completion of the experiment, the body weight, body length, skin color, etc. of each goldfish were measured. There was no difference between the filtering materials (10) of Example 1 or 2 and that of Comparative Example 1.

This finding demonstrates that the cortex of Japanese cedar and/or Japanese cypress has no physiologically adverse effect on fish.

EXPERIMENTAL EXAMPLE 2

The spirogyra controlling performance of the cortex of Japanese cedar and/or Japanese cypress in water culture was rated.

Figure 2:
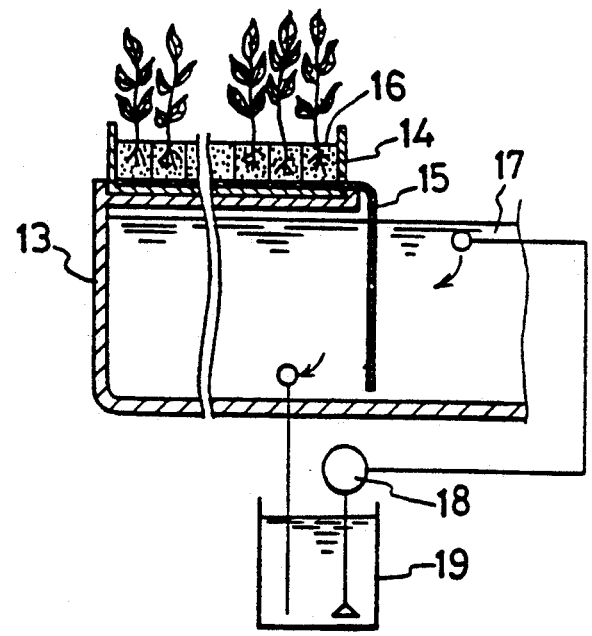
FIG. 2 is a shematic explaining the experimental method of Experimental Example 2.
Figure 3:
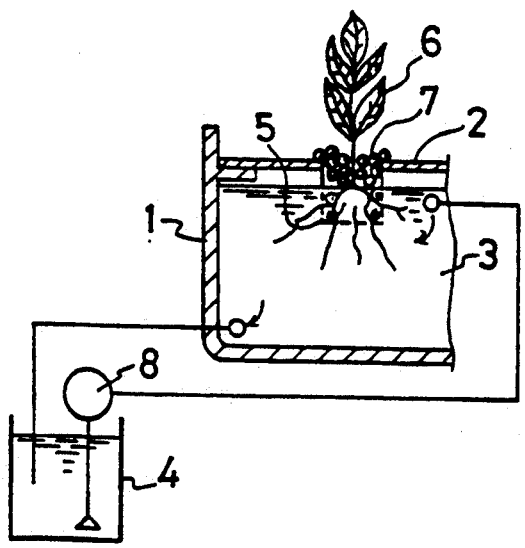
FIG. 3 is a schematic explaining a prior art method of controlling spirogyra in water culture.

The experiment was conducted as illustrated in FIG. 2. Specifically, a water culture tray (14) was placed above the solution chamber (13). Solution absorbing cloth (15) was placed on the inner base of the tray (14), and block medium (16) of Example 4 through 6 or Comparative Example 2 comprising only urethane resin, planted with Japanese honewort or celery, was placed on the absorbing cloth. Solution (17) was circulated from the solution tank (19) to the solution chamber (13) via a circulatory pump (18) to feed the solution (17) to the block medium (16) through the solution chamber (13) via the solution absorbing cloth (15) for 4 consecutive weeks.

The spirogyra controlling performance was rated by visually monitoring the state of occurrence or development of spirogyra once weekly.

The results of assessment are shown in Table 2.

As seen in Table 2, spirogyra occurred and showed noticeable development in Comparative Example 2, while spirogyra did not occur until 3 weeks following initiation of the experiment in Example 4, and did not occur at all, even after 4 weeks, in Example 5 or 6.

This finding demonstrates that the cortex of Japanese cedar and/or Japanese cypress possesses high capability for spirogyra control in water culture.

After completion of the experiment, the radishes, Japanese honeworts and celeries grown were collected and their odor evaluated. Samples collected from Comparative Example 2 were malodorous, while those collected from Examples 4 through 6 had no malodor.

This finding demonstrates that malodor in grown plants can be prevented by controlling spirogyra with the cortex of Japanese cedar and/or Japanese cypress.

Also, when the spirogyra controlling and deodorant composition of Example 3 was used as a filter for eutrophicated pond water and for smelling drinking water, contaminants were removed and clear odorless beautiful pond water and odorless drinking water were obtained, respectively.

TABLE 1

|  | 1W | 2W | 3W | 4W | 5W |
|---|---|---|---|---|---|
| Example 1 | − | − | − | − | − |
| Example 2 | − | − | − | − | − |
| Example 3 | − | − | − | − | ± |
| Comparative Example 1 | + | ++ | +++ | ++++ | +++++ |

TABLE 2

|  | 1W | 2W | 3W | 4W |
|---|---|---|---|---|
| Example 4 | − | − | ± | ++ |
| Example 5 | − | − | − | − |
| Example 6 | − | − | − | − |
| Comparative Example 2 | + | ++ | ++++ | +++++ |

TABLE 3

|  | 1W | 2W | 3W | 4W | 5W |
|---|---|---|---|---|---|
| Example 7 | − | − | − | − | ± |
| Example 8 | − | − | − | − | ± |
| Example 9 | − | − | − | − | ± |

TABLE 3-continued

|  | 1W | 2W | 3W | 4W | 5W |
|---|---|---|---|---|---|
| Example 10 | − | − | − | − | − |
|  | − | − | − | − | − |
| Example 11 | − | − | − | − | − |
|  | − | − | − | − | − |
| Comparative Example 3 | + | ++ | +++ | ++++ | +++++ |

In Tables 1, 2 and 3, 1W through 5W or 1W through 4W respectively represent durations of 1 to 5 weeks and 1 to 4 weeks; − indicates that spirogyra did not occur; + through +++++ indicate the occurrence of spirogyra and the degree of its development.

EXPERIMENTAL EXAMPLE 3

1 g (30000 times) and 3 g (10000 times) of each of Examples 7 through 11 were added and uniformly agitated, whereby the same test as in the above-mentioned Experimental Example 1 was conducted. The results of assessment are shown in Table 3. Although those Examples could not present so good results as Examples 1 to 3, they could show quite good results. Further, in this case, if emulsifier is added to the extract in the amount of 3 to 20%, preferably 5 to 10%, it is uniformly dispersed when diluting with water. As for the emulsifier, normally nonionic emulsifier, anionic emulsifier and cationic emulsifier, and mixture of these emulsifier can be utilized.

What is claimed is:

1. A filter for preventing occurrence of spirogyra and bad odor comprising the cortex of Japanese cedar, Japanese cypress, or a mixture thereof in a feathery form or in a milled form wherein the feathery or milled form of the cortex is molded into a plate.

2. A solid bedding soil for preventing occurrence of spirogyra and bad odor comprising the cortex of Japanese cedar, Japanese cypress, or a mixture thereof in a feathery form or in a milled form wherein the feathery or milled form of the cortex is bound into a solid.

3. A spirogyra controlling and deodorant composition consisting essentially of the cortex of Japanese cedar, Japanese cypress, or a mixture thereof in a feathery form or in a milled form.

4. A spirogyra controlling and deodorant composition consisting essentially of the cortex of Japanese cedar, Japanese cypress, or a mixture thereof in the form of an extract of said cortex.

* * * * *